United States Patent
Lee et al.

(10) Patent No.: US 11,207,363 B2
(45) Date of Patent: Dec. 28, 2021

(54) PHARMACEUTICAL COMPOSITION FOR PREVENTION OR TREATMENT OF ALZHEIMER'S DISEASE, COMPRISING MOUNTAIN-CULTIVATED GINSENG EXTRACT

(71) Applicants: KANGWON NATIONAL UNIVERSITY INDUSTRY COOPERATION FOUNDATION, Chuncheon-si (KR); Sang Il Lee, Suwon-si (KR)

(72) Inventors: Sang Il Lee, Suwon-si (KR); Hyoung Chun Kim, Chuncheon-si (KR); Sung Kwon Ko, Sejong (KR); Eun Joo Shin, Chuncheon-si (KR)

(73) Assignees: KANGWON NATIONAL UNIVERSITY INDUSTRY COOPERATION FOUNDATION, Chuncheon-si (KR); Sang Il Lee, Suwon-si (KR)

( * ) Notice: Subject to any disclaimer, the term of this patent is extended or adjusted under 35 U.S.C. 154(b) by 94 days.

(21) Appl. No.: 16/608,922

(22) PCT Filed: Apr. 26, 2018

(86) PCT No.: PCT/KR2018/004864
§ 371 (c)(1),
(2) Date: Oct. 28, 2019

(87) PCT Pub. No.: WO2018/199654
PCT Pub. Date: Nov. 1, 2018

(65) Prior Publication Data
US 2021/0113639 A1    Apr. 22, 2021

(30) Foreign Application Priority Data

Apr. 28, 2017 (KR) .................. 10-2017-0055100

(51) Int. Cl.
*A61K 36/258* (2006.01)
*A61P 25/28* (2006.01)

(52) U.S. Cl.
CPC ............ *A61K 36/258* (2013.01); *A61P 25/28* (2018.01); *A61K 2236/333* (2013.01)

(58) Field of Classification Search
CPC ...... A23L 33/105; A61K 36/258; A61P 25/28
See application file for complete search history.

(56) References Cited

FOREIGN PATENT DOCUMENTS

| KR | 10-0452555 B1 |   | 10/2004 |
| KR | 20120001977 A | * | 1/2012 |
| KR | 10-2012-0022293 A |   | 3/2012 |

\* cited by examiner

*Primary Examiner* — Aaron J Kosar
(74) *Attorney, Agent, or Firm* — Vorys, Sater, Seymour and Pease LLP; Mih Suhn Koh

(57) ABSTRACT

The present invention provides a pharmaceutical composition for preventing or treating Alzheimer's disease and a food composition for relieving symptoms of Alzheimer's disease, which comprise a mountain-cultivated ginseng extract. The composition comprising the mountain-cultivated ginseng extract of the present invention is beneficially used as a pharmaceutical composition for preventing or treating Alzheimer's disease in the medical field for the treatment of Alzheimer's disease or as a food composition for relieving the symptoms of Alzheimer's disease.

4 Claims, 11 Drawing Sheets

[Figure 1]

\#: Behavioral tests (Y-maze, Novel Object Recognition, Passive Avoidance)
§: Sacrifice

*p < 0.01 vs. no treatment
p < 0.05 vs. mice-treated with Field-cultivated ginseng

PHARMACEUTICAL COMPOSITION FOR PREVENTION OR TREATMENT OF ALZHEIMER'S DISEASE, COMPRISING MOUNTAIN-CULTIVATED GINSENG EXTRACT

TECHNICAL FIELD

The present invention relates to a pharmaceutical composition for preventing or treating Alzheimer's disease, and more particularly to a pharmaceutical composition for preventing or treating Alzheimer's disease, which comprises a mountain-cultivated ginseng extract.

BACKGROUND ART

Mountain-cultivated ginseng has high content of organic germanium and saponin, which have excellent pharmacological action, and thus has the effect of promoting health of people of all ages, from children to the elderly. Mountain-cultivated ginseng is ginseng produced in mountainous areas without artificial facilities, and grows slowly because it is cultivated naturally in the same place for more than 7 years. As for the cultivation area of the mountain-cultivated ginseng, cool mountain areas with summer temperatures of 20 to 25° C., woody shady areas including trees more than 20 years old occupying 80 to 90% thereof, weakly acidic sandy loam that is rich in organic matter and has good drainage, and areas other than ridges facing the east, north, and northwest are demanded. Accordingly, growing conditions are difficult to satisfy.

Ginseng is artificially managed by installing rain shelter facilities in manmade fields and is classified into 4-, 5- and 6-year-old ginseng according to the cultivation period thereof. In order to increase the quantity of ginseng, fertilizers, compost, and pesticides are appropriately used. Accordingly, the ginseng is thick. In contrast, mountain-cultivated ginseng may be cultivated for about 7 to 10 years in a cultivation area of the mountain. That which is grown over 11 years is classified as ginseng grown in the wild or wild ginseng. Since the type of saponins and biological tissue components of ginseng depend on the number of years of growth, the content of useful components increases with an increase in the number of years of growth thereof. However, ginseng cannot be cultivated in the field for more than 7 years due to the limited availability of arable areas, so the clearest classification criteria thereof is known to be the number of years of growth.

Mountain-cultivated ginseng is grown in shady and humid places around which birch and lacquer trees are present in the deep mountains, in particular, is grown only in half-shaded and outlying places, and is harvested 6 to 30 years after planting wild ginseng seeds in the mountains and subsequent culture. Most ginseng has three to seven heads (outcorp), but mountain-cultivated ginseng has more heads due to the age thereof and also has a body surrounded by a ring-shaped girdle which is not found in ginseng. The roots of ginseng are thick and short, but the roots of mountain-cultivated ginseng are thin and long, sometimes over 1 m long. The lifespan of mountain-cultivated ginseng is 50 years to several hundred years depending on soil and climatic conditions, but the lifespan of ginseng is a maximum of about 20 years. Further, the mountain-cultivated ginseng is characterized by a strong scent compared to ginseng. The various efficacies of ginseng are: liver function activation, blood-sugar-lowering action, diabetes symptom relief, inhibition of cancer cell growth, lowering blood pressure, preventing arteriosclerosis, activating immune functions in the body, preventing anemia, promoting metabolism in the body, promoting learning ability and memory due to the stimulation effect on central nerves, and 50 mg/kg and fatigue relief effects.

In the comparative study of ginseng saponin of mountain-cultivated ginseng and cultivated ginseng, the ratio of protopanaxadiol and panaxatriol (protopanaxatriol) in the mountain-cultivated ginseng was found to be 3.25, higher than 2.45 in the 4-year-old cultivated ginseng and 2.18 in the 6-year-old cultivated ginseng. In particular, the ratio of ginsenoside Rb1 and Rg1 in the mountain-cultivated ginseng was reported to be 10.22, which was higher than 3.51 in the 4-year-old cultivated ginseng and 4.86 in the 6-year-old cultivated ginseng. In addition, it was reported that the content of Rd and Re was higher in the mountain-cultivated ginseng than in the cultivated ginseng (Analysis of Ginsenoside Composition of Woods-Grown Ginseng Roots, Sung Tai Han, Cha Gyun Shin, Byung Wook Yang, Young Tae Hahm, Uy Dong Sohn, Byung Ok Im, Soon Hyun Cho, Boo Yong Lee and Sung Kwon Ko, Food Science & Biotechnology, 16(2), 281-284, 2007).

Alzheimer's disease is a disease having a histological feature in which hippocampus and cortex areas exhibit amyloid plaque and neurofibrillary tangles (Neuron, 6, 487-498), and the most important process in the etiology of Alzheimer's disease is the accumulation of non-aqueous beta-amyloid (β-amyloid, Aβ) peptides. The content of Aβ (1-40) and Aβ (1-42) is highest in the non-aqueous beta-amyloid peptide, and Aβ (1-42) has been proven to be more toxic than Aβ (1-40) because Aβ (1-42) more easily aggregates into amyloid plaque compared to Aβ (1-40) (Acta Biolchm. Pol., 52, 417-423). In addition, differences in genes such as amyloid precursor protein (APP), presenilin (PS)-1, PS-2, and apolipoprotein, and oxidative toxicity are known to be involved in the etiology of Alzheimer's disease (BBA, 2007, 285-297), which has been confirmed by establishing animal models suffering from Alzheimer's disease using various genetically modified animals, for example, APP expressing mice, or through central administration of toxic Aβ peptides.

Oxidative damage due to the accumulation of non-aqueous Aβ is known as one of the major etiologies of Alzheimer's disease, and an increase in an oxidative damage indicator (Neurochem. Res. 33, 450-458; Neurotox. Rex. 2, 167-168) and endogenous abnormalities of antioxidant systems (Neurotox. Rex. 2, 167-168) have been reported in the brain tissue of Alzheimer's disease patients. This phenomenon has also been reported in an animal model suffering from Alzheimer's disease (Behav. Brain Res., 155, 185-196; J. Neurosci., 27, 5394-5404). In addition, the resultant damage and function deterioration of the cholinergic system of the hippocampus and cortex areas contribute to a decrease in cognitive memory, which is a characteristic symptom of Alzheimer's disease (Neurology 51, S18-S29; Curr. Alzheimer Res. 1, 241-248).

Meanwhile, as a prior art for the prevention or treatment of Alzheimer's disease, Korean Laid-Open Patent Application No. 10-2005-0101537 discloses the administration of 3-amino-1-propanesulfonic acid and a neuroprotective agent or a neurotrophic agent in combination for the purpose of treating amyloid-β-related diseases including Alzheimer's disease. Further, Korean Laid-Open Patent Application No. 10-2012-48105 discloses a pharmaceutical composition including ursodeoxycholic acid and a ginkgo leaf extract combined therein to thus secure a synergistic therapeutic effect on Alzheimer's disease. In addition, various inventions related to a composition or medical use for treating Alzheimer's disease have been made, but there is still a need to develop various drugs useful for treating Alzheimer's disease.

DISCLOSURE

Technical Problem

The present inventors have studied herbal extracts exhibiting anti-Alzheimer's efficacy, and found that a mountain-cultivated ginseng extract is excellent in the anti-Alzheimer's efficacy in animal models suffering from Alzheimer's disease.

Accordingly, an object of the present invention is to provide a pharmaceutical composition for preventing or treating Alzheimer's disease, which comprises a mountain-cultivated ginseng extract.

Technical Solution

According to an aspect of the present invention, there is provided a pharmaceutical composition for preventing or treating Alzheimer's disease, which comprises a mountain-cultivated ginseng extract.

In an embodiment, the extract may be a mixture of an ethanol extract and a water extract, and preferably a mixture of extracts obtained using ethanol and water, so that an ethanol extract and a water extract are mixed at a ratio of 1:1 (volumetric ratio).

In an embodiment, the Alzheimer's disease may exhibit an Iba-1-IR positive reaction or the production of amyloid plaque.

According to another aspect of the present invention, there is provided a food composition for relieving the symptoms of Alzheimer's disease, which comprises a mountain-cultivated ginseng extract.

In an embodiment, the extract may be a mixture of an ethanol extract and a water extract, and preferably a mixture of extracts obtained using ethanol and water so that an ethanol extract and a water extract are mixed at a ratio of 1:1 (volumetric ratio).

In an embodiment, the Alzheimer's disease may exhibit an Iba-1-IR positive reaction or the production of an amyloid plaque.

Advantageous Effects

According to the present invention, a mountain-cultivated ginseng extract was found to have a ginsenoside content higher than that of a field-cultivated ginseng extract. Further, the mountain-cultivated ginseng extract was found to be excellent in effects of increasing a space working memory, visual recognition memory, and associative learning, improving cholinergic nervous system functions of the hippocampus, and inhibiting an Iba-1-IR positive reaction of microglia and the production of amyloid plaque in animal models suffering from Alzheimer's disease compared to the field-cultivated ginseng extract. Accordingly, the mountain-cultivated ginseng extract was found to have superior anti-Alzheimer's efficacy compared to the field-cultivated ginseng extract.

Therefore, it is possible to helpfully use a composition including a mountain-cultivated ginseng extract of the present invention as a pharmaceutical composition for preventing or treating Alzheimer's disease or as a food composition for relieving the symptoms of Alzheimer's disease.

DESCRIPTION OF DRAWINGS

FIGS. 9A and 9B are a photograph and a graph showing the pharmacological effects of a mountain-cultivated ginseng extract and a field-cultivated ginseng extract on the production of amyloid plaque in hippocampus and cerebral cortex tissues of APPswe/PS1dE9 double-expressing mouse

[*: p<0.01 vs. control group; #: p<0.05 vs. group treated with field-cultivated ginseng extract].

BEST MODE

The present invention provides a pharmaceutical composition for preventing or treating Alzheimer's disease, which comprises a mountain-cultivated ginseng extract.

In an embodiment of the present invention, the extract may be a mixture of an ethanol extract and a water extract, and preferably a mixture of extracts obtained using ethanol and water so that an ethanol extract and a water extract are mixed at a ratio of 1:1 (volumetric ratio), without limitation thereto.

In the embodiment, the Alzheimer's disease may exhibit an Iba-1-IR positive reaction or the production of amyloid plaque.

The pharmaceutical composition of the present invention may comprise a pharmaceutically acceptable carrier, and the pharmaceutical composition may be prepared in the form of oral formulations such as powders, granules, tablets, capsules, suspensions, emulsions, syrups, and aerosols, external preparations, suppositories, and sterile injectable solutions according to typical methods. The pharmaceutically acceptable carrier includes lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methyl hydroxybenzoate, propyl hydroxybenzoate, talc, magnesium stearate, or mineral oil. Further, the pharmaceutically acceptable carrier includes a diluent or an excipient such as a filler, an extender, a binder, a wetting agent, a disintegrating agent, and a surfactant. Examples of an oral solid preparation thereof include a tablet, a pill, a powder, a granule, and a capsule. The solid preparation may comprise at least one excipient, for example, starch, calcium carbonate, sucrose, lactose, or gelatin, and a lubricant such as magnesium stearate and talc. Examples of an oral liquid preparation thereof include a suspension, an oral liquid, an emulsion, and a syrup, and the oral liquid preparation may include a diluent such as water and liquid paraffin, a wetting agent, a sweetener, a flavoring agent, or a preservative. Examples of a parenteral preparation thereof include a sterile aqueous solution, a non-aqueous solvent, a suspension, an emulsion, a lyophilized preparation, and a suppository. As the non-aqueous solvent and the suspension, propylene glycol, polyethylene glycol, vegetable oil such as olive oil, and injectable esters such as ethyl oleate are included. As the base of the suppository, Witepsol, macrogol, tween 61, cacao butter, laurinum, and glycerogelatin may be used.

The dosage of the extract contained in the pharmaceutical composition of the present invention depends on the condition and weight of the patient, the progression of the disease, the form of the drug, and the route and duration of administration, but may be appropriately selected by those skilled in the art. For example, the extract may be administered at a dose of 0.0001 to 1000 mg/kg and preferably 0.01 to 1000 mg/kg a day, and the administration may be performed once a day or may be dividedly performed several times a day.

The pharmaceutical composition of the present invention may be administered to mammals, such as rats, mice, livestock, and humans, through various routes, for example, orally, intraperitoneally, rectally, intravenously, intramuscularly, subcutaneously, by intrauterine dural injection, or by intracerebrovascular (intracerebroventricular) injection.

Further, the present invention provides a food composition for relieving symptoms of Alzheimer's disease, which comprises a mountain-cultivated ginseng extract.

In an embodiment, the extract may be a mixture of an ethanol extract and a water extract, and preferably a mixture of extracts obtained using ethanol and water so that an ethanol extract and a water extract are mixed at a ratio of 1:1 (volumetric ratio).

In the embodiment, the Alzheimer's disease may exhibits an Iba-1-IR positive reaction or the production of amyloid plaque.

MODE FOR INVENTION

Hereinafter, the present invention will be described in more detail with reference to Examples. However, the following Examples are intended to illustrate the present invention, but the scope of the present invention is not limited thereto.

EXAMPLE

1. Extraction and Component Analysis of Mountain-Cultivated Ginseng (1) Method for Extracting Mountain-Cultivated Ginseng 1.5 kg of a mountain-cultivated ginseng was added to 20 L of ethanol and extracted using an ultrasonic treating device (KODO, Hwaseong, Korea, output 1,200 W, frequency 28 KHz) at 65° C. for 48 hours, followed by filtering. 20 L of distilled water was added to the residue, and an additional filtrate filtered by extraction at 100° C. for 10 hours was combined with the filtrate that was previously obtained, followed by concentration under reduced pressure, thus obtaining a mountain-cultivated ginseng extract (essence).

The extract of the field-cultivated ginseng (6 years old), harvested in Eumseong-gun, was manufactured under the above-described conditions.

(2) Preparation of Crude Saponin 50 ml of diethyl ether was added to the mountain-cultivated ginseng essence obtained above and was subjected to repeated ultrasonic extraction three times at room temperature for 1 hour, followed by centrifugation to thus remove a supernatant. 50 ml of water-saturated butanol was added to the residue, and ultrasonic extraction at room temperature for 2 hours was repeated three times. The butanol layer obtained using centrifugation was collected and concentrated under reduced pressure, thus obtaining crude saponin.

(3) HPLC Analysis

The essence obtained above was directly compared to a specimen so that a ginseng saponin content and a composition were analyzed by repeating an experiment three times for each sample to confirm the reproducibility of the results according to a typical method. As the specimen, ginsenoside having a purity of 99% or more purchased from Chromadex (U.S.A.) and Ambo Research Institute (Korea) was used. Analysis was performed using an HPLC apparatus (Waters 1525 binary HPLC system, Waters, USA) and a column (Eurospher 100-5 C18, 250*3 mm). As a mobile phase, acetonitrile (HPLC grade, Sigma, U.S.A.) and distilled water for HPLC were used in combination. The ratio of acetonitrile was sequentially increased from 17% (0 min) to 25% (20 min), 42% (38 min), 100% (42 min), and 100% (52 min). The ratio was finally adjusted to 17%. The development temperature was room temperature, the flow rate was 0.8 ml per minute, and the chromatogram was observed at 203 nm using a detector (uv/vis Waters 2487 Dual A Absorbance Detector, Waters, U.S.A.).

(4) Comparison of Ginsenoside Compositions of Mountain-Cultivated Ginseng Extract and Field-Cultivated Ginseng Extract The results of analysis of the ginsenoside composition of the mountain-cultivated ginseng extract and the field-cultivated ginseng extract are shown in the following Table 1. The ginsenoside content was measured to be higher in the mountain-cultivated ginseng extract than in the field-cultivated ginseng extract.

TABLE 1

| Ginsenoside | Mountain-cultivated ginseng | Field-cultivated ginseng |
| --- | --- | --- |
| Rb1 | 0.990 ± 0.019 | 0.889 ± 0.018 |
| Rb2 | 0.253 ± 0.002 | 0.255 ± 0.002 |
| Rc | 0.412 ± 0.006 | 0.295 ± 0.001 |
| Rd | 0.205 ± 0.004 | 0.067 ± 0.000 |
| Re | 0.376 ± 0.009 | 0.244 ± 0.004 |
| Rf | 0.064 ± 0.002 | 0.040 ± 0.000 |
| Rg1 | 0.338 ± 0.013 | 0.294 ± 0.003 |
| Total | 2.639 | 2.085 |

2. Preparation of Animals and Extract Treatment (1) Preparation of Animals

All animals were treated in compliance with the NIH Guide for the Welfare and Use of Experimental Animals (NIH Publication No. 85-23, 1985; www.dels.nas.edu/ila). The present invention was carried out in accordance with the ILAR (Institute for Laboratory Animal Research) guidelines for the Welfare and Use of Experimental Animals.

As an animal model suffering from Alzheimer's disease, 6-month-old APP/PS1 (amyloid precursor protein/presenilin-1, APPswe/PS1dE9) double-expressing (double transgenic) mice were used (The Jackson Laboratory, Bar Harbor, Mass., USA), 12:12 h light:dark cycles were maintained, and the mice were allowed to feed freely (ad libitum).

(2) Extract Treatment

Figure 1:
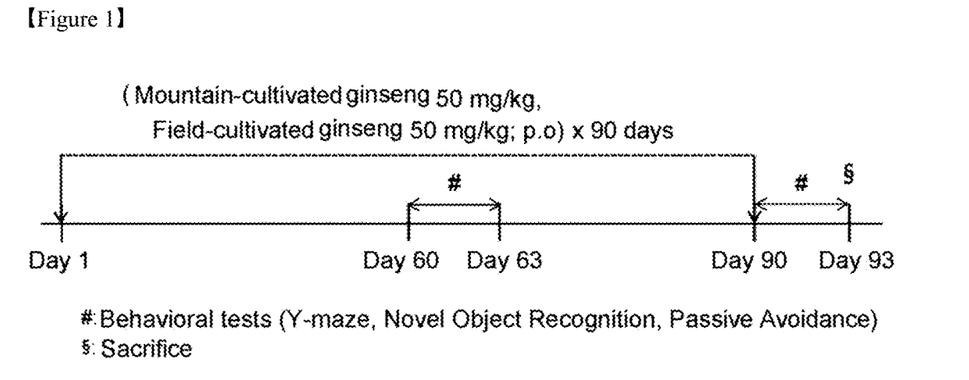
FIG. 1 is a schematic view showing the process of treatment and experimentation on a mountain-cultivated ginseng extract using an animal model suffering from Alzheimer's disease [a group treated with a mountain-cultivated ginseng extract (n=8), a group treated with a field-cultivated ginseng extract (n=8), and a control group (No treatment, n=6)]

FIG. 1 shows a process of treating experimental animals with a mountain-cultivated ginseng extract. Each extract (mountain-cultivated ginseng extract or field-cultivated ginseng extract, 50 mg/kg, p.o.) was administered to the experimental animals for 90 days, and behavioral evaluation was performed on the 60th to 63rd day and 90th to 93rd day (Y-maze experiment, novel object recognition experiment, and passive avoidance test).

In the period during which the behavioral evaluation was performed, in order to prevent each extract from directly affecting the behavior, the extracts were administered after the behavioral evaluation was over. One day after the end of the behavioral evaluation, the animals were sacrificed to obtain hippocampus and cortex tissues.

The experiment was performed through classification into three groups, namely a group treated with a mountain-cultivated ginseng extract (n=8), a group treated with a field-cultivated ginseng extract (n=8), and a control group (No treatment, n=6), and n was 6 in each group.

3. Anti-Alzheimer's Efficacy Evaluation (1) Y-Maze Experiment

The Y-maze experiment was performed as described in a prior art document [J. Alzheimers Dis. (31, 207-223)]. The Y-maze includes a Y-shaped arm and a black plastic box that is 25 cm long, 14 cm high and 5 cm wide. The mouse was placed at the end of one arm and allowed to move freely between arms for 8 minutes. The number of times the mouse entered each arm was checked using a video camera. The evaluation indicator of the space alternation behavior was compared to that of the control group, and one point was awarded when the mouse entered all three arms. The alternation score of the mouse was converted to 100% by dividing the score actually obtained by the mouse by the highest possible alternation score.

(2) Novel Object Recognition Experiment

A novel object recognition experiment was performed as described in a prior art document [Learn. Mem. (14, 117-125)]. On the first day, the mouse was placed in a box 40 cm×40 cm×30 cm in size and allowed to move freely for 10 minutes to become accustomed thereto. On the second day, two objects were placed in the box and the reaction time for each object was recorded. 24 hours after this time point, one of the two objects was replaced with a novel object and then the reaction time for the novel object was recorded.

(3) Passive Avoidance Test

A passive avoidance test was performed using a Gemini Avoidance System (San Diego Instrument, San Diego, Calif.) as described in a prior art document [Behav. Brain Res. (155, 185-196)]. The system included two spaces with a shock generator on the floor thereof, and a guillotine door was provided between the two spaces. In the acquisition trial, the mouse was placed in one space (start chamber) and then allowed to become accustomed thereto for 20 seconds. After 20 seconds, when a light was turned on in the space in which the mouse was placed, the guillotine door was opened between the spaces. As soon as the mouse entered the other space, in which a light was not turned on, the guillotine door was closed and an electric shock was applied (0.3 mA, 3 s, once). After 24 hours, in a retention test (retention trial), the mouse was returned to the start chamber, a light was turned on, and the time taken for the mouse to move to the other space (step-through latency) was recorded (up to 300 seconds).

(4) Measurement of Choline Acetyltransferase Activity (ChAT Activity), Acetylcholine Level (Ach Level), and Acetyl Cholinesterase Activity (AchE Activity)

24 hours after the passive avoidance test was finished, the hippocampus and cortex areas of the mouse were cut and pulverized with an ultrasonic tissue pulverizing device (Bronson Sonic, NY). After centrifugation at 10,000 g at 4° C. for 20 minutes, the supernatant was collected to measure the concentration of acetylcholine and the activities of acetyl cholinesterase and choline acetyltransferase.

The ACh value and the AChE activity in the hippocampus and cortical tissues were measured using a kit (Amplex® Red Acetylcholine/Acetylcholinesterase Assay Kit, Molecular Probes, Inc., Eugene, KOR) according to the manufacturer's protocol.

The ChAT activity was measured according to the method of Mehta et al. [Mehta H, Haobam R, Usha R, Mohanakumar K P. Evidence for the involvement of central serotonergic mechanism in cholinergic tremor induced by tacrine in Balb/c mice. Behav. Brain Res. 2005; 163: 227-236.] That is, 25 µl of a solution of 0.5 M sodium phosphate buffer (pH 7.2), acetyl-CoA (6.2 mM), choline chloride (1 M), neostigmine sulfate (0.76 mM), NaCl (3 M), and EDTA (1.1 mM) was taken, and distilled water was then add thereto to adjust the volume to 400 µl. The resultant solution was pre-incubated at 37° C. for 5 minutes, and then 100 µl of the sample was added thereto, followed by incubation at 37° C. for 20 minutes.

After boiling the sample for 2 minutes to terminate the reaction, 1 ml of distilled water was added thereto, and centrifugation was performed to remove denatured protein. Thereafter, 1 ml of the supernatant was added to a test tube containing 30 µl of dithiopyridine (4,4'-dithiopyridine, 10 mM). The absorbance thereof was measured at 324 nm after 15 minutes.

The ChAT activity was expressed as coenzyme nmol/hr·g protein. The protein concentration was measured using a BCA protein assay reagent (Pierce, Rockford, Ill., U.S.A.) according to the manufacturer's protocol.

(5) Immunocytology of Microglia

With respect to immunocytology, the method described in a prior art document (Shin et al., 2014, Mol. Neurobiol. 50, 60-75) was used. Mice were percutaneously perfused with 50 mL of ice-cold PBS (10 mL/10 g body weight) and then 4% paraformaldehyde (20 mL/10 g body weight). The brains thereof were removed and stored overnight in 4% paraformaldehyde. The brain was cut into coronal sections mm thick. The brain sections were blocked with PBS containing 0.3% hydrogen peroxide for 30 minutes and then incubated for 20 minutes in 0.4% Triton X-100 and 1% normal-serum-containing PBS.

(6) Beta-Amyloid

The production of amyloid plaque in hippocampus and cortex tissues of APPswe/PS1dE9 double-expressing mice was evaluated using an immunohistochemical staining method. Perfusion was performed, and the brain tissue fixed with 4% p-formaldehyde was cut into sections 40 µm thick. The sections were exposed to 0.2% Triton X-100 for 15 minutes before incubation in an Aβ (1-42) antibody (Invitrogen, Carlsbad, Calif., U.S.A.) overnight. The sections were then incubated in 4% normal goat serum. After one night, the sections were incubated in a secondary antibody for 1 hour, and immunostaining was performed using 3,3-diaminobenzidine as a chromogen. In each step, washing with PBS (pH 7.4) was performed.

4. Results (1) Y-Maze Experiment

Figure 2:
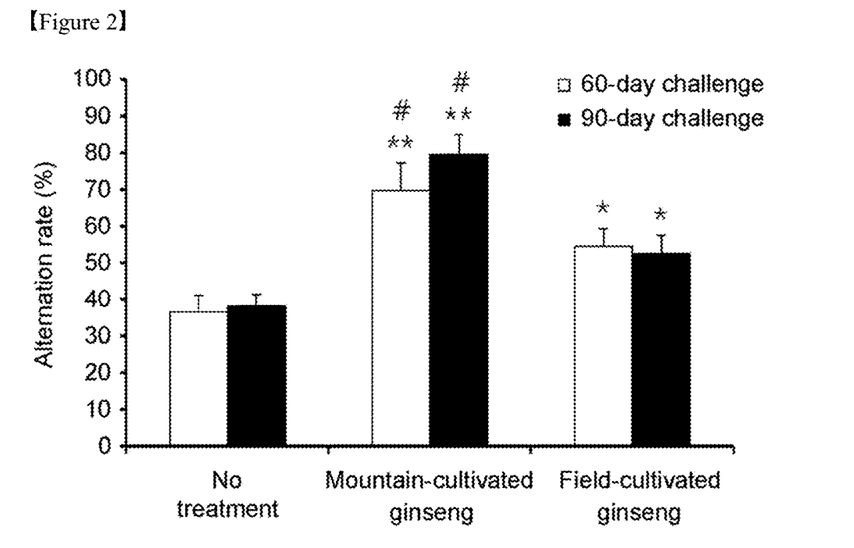
FIG. 2 is a graph showing the results of evaluation of a control group, a group treated with a mountain-cultivated ginseng extract, and a group treated with a field-cultivated ginseng extract in a Y-maze experiment on the animal model suffering from Alzheimer's disease [*: $p<0.05$, **: $p<0.01$ vs. control group; #: $p<0.05$ vs. group treated with field-cultivated ginseng extract]

Administration of the mountain-cultivated ginseng extract to the mouse significantly increased the space alternation behavior (50 mg/kg, $P<0.05$) (FIG. 2) compared to the field-cultivated ginseng extract. With respect to this increasing tendency, an increase in space alternation behavior was decreased as the administration period of the extract was increased in the case of the field-cultivated ginseng extract, but the increase in space alternation behavior was increased as the administration period was increased in the case of the mountain-cultivated ginseng extract. The results indicate that the mountain-cultivated ginseng extract has superior efficacy of increasing the space working memory compared to the field-cultivated ginseng extract.

(2) Novel Object Recognition Experiment

Figure 3:
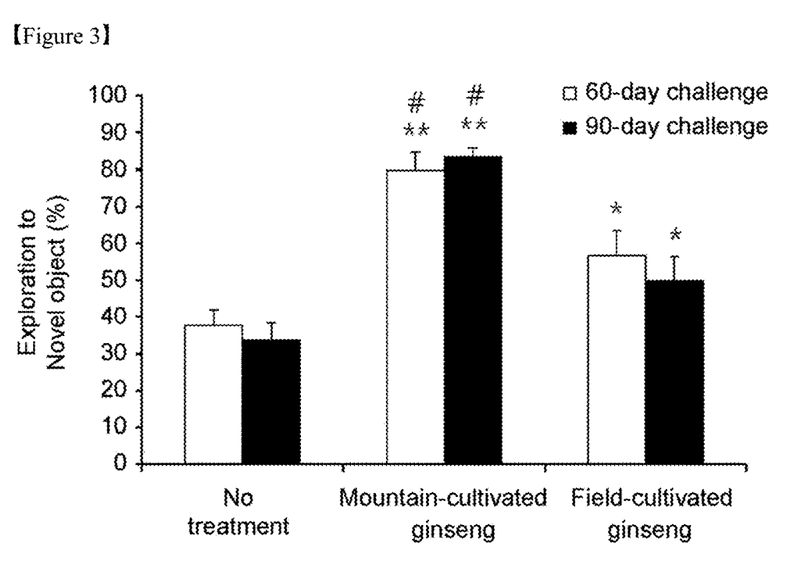
FIG. 3 is a graph showing the results of evaluation of a control group, a group treated with a mountain-cultivated ginseng extract, and a group treated with a field-cultivated ginseng extract in a novel object recognition experiment on the animal model suffering from Alzheimer's disease [*: $p<0.05$, **: $p<0.01$ vs. control group; #: $p<0.05$ vs. group treated with field-cultivated ginseng extract]

Administration of the mountain-cultivated ginseng extract to the mouse significantly increased the searching behavior for novel objects in a novel object recognition experiment ($P<0.05$) compared to the field-cultivated ginseng extract, which means an increase in visual recognition memory (FIG. 3). With respect to this increasing tendency, an increase in the searching behavior for novel objects was decreased as the administration period of the extract was increased in the case of the field-cultivated ginseng extract, but the increase in searching behavior for novel objects was increased as the administration period was increased in the case of the mountain-cultivated ginseng extract. The results indicate that the mountain-cultivated ginseng extract has significant pharmacological efficacy in increasing visual recognition memory compared to the field-cultivated ginseng extract.

(3) Passive Avoidance Test

Figure 4:
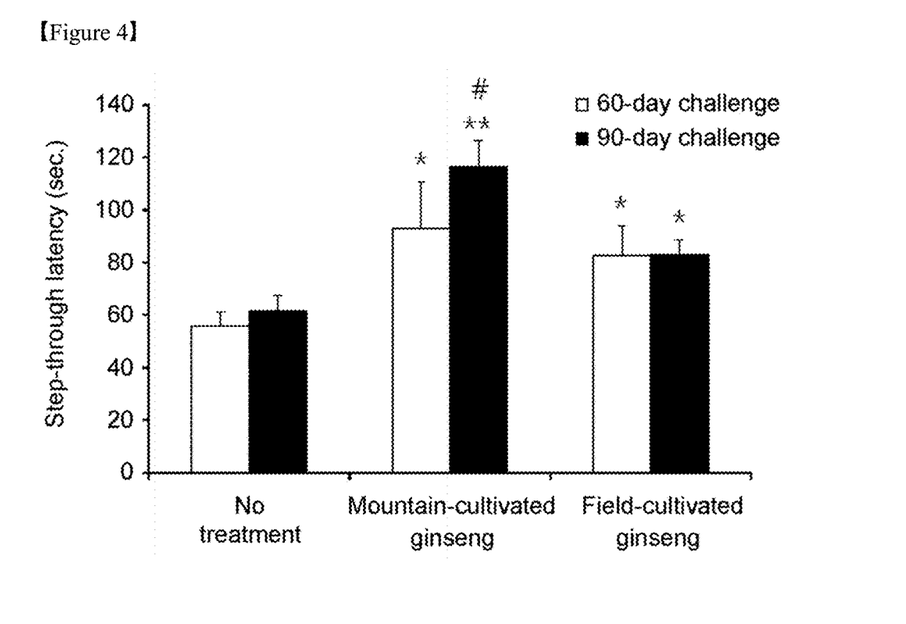
FIG. 4 is a graph showing the results of evaluation of a control group, a group treated with a mountain-cultivated ginseng extract, and a group treated with a field-cultivated ginseng extract in a passive avoidance test on the animal model suffering from Alzheimer's disease [*: $p<0.05$, **: $p<0.01$ vs. control group; #: $p<0.05$ vs. group treated with field-cultivated ginseng extract]

Administration of the mountain-cultivated ginseng extract to the mouse significantly increased the step-through latency of movement toward the dark room in a passive avoidance reaction experiment ($P<0.05$) compared to the field-cultivated ginseng extract, which means an increase in associative learning (FIG. 4). With respect to this increasing tendency, an increase in step-through latency was maintained as the administration period of the extract was increased in the case of the field-cultivated ginseng extract, but the increase in step-through latency was increased as the administration period was increased in the case of the mountain-cultivated ginseng extract. The results indicate that the mountain-cultivated ginseng extract has significant pharmacological efficacy in increasing associative learning compared to the field-cultivated ginseng extract.

Figure 5:
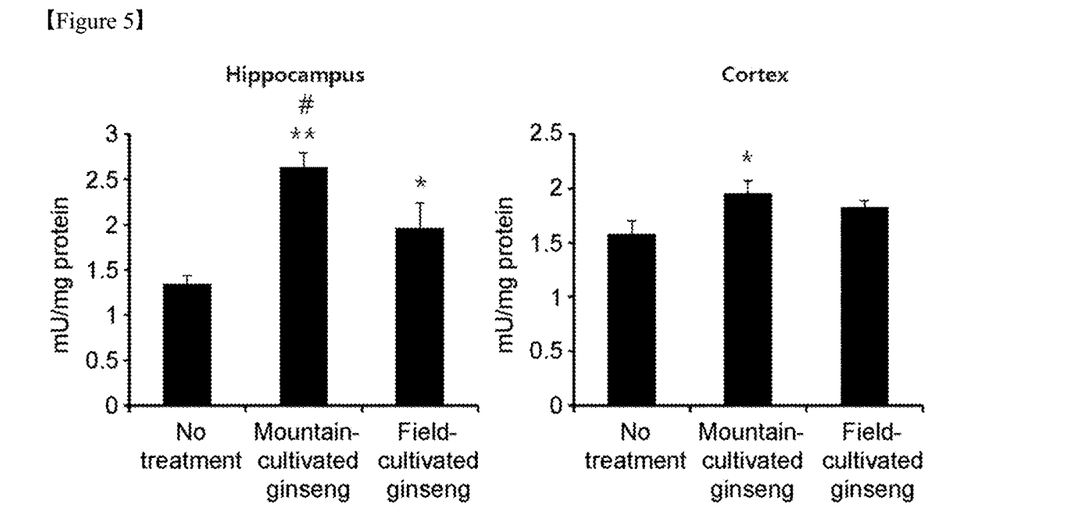
FIG. 5 is a graph showing the results of measurement of the choline acetyltransferase activity (ChAT activity) in hippocampi and cerebral cortexes (cortex) of a control group, a group treated with a mountain-cultivated ginseng extract, and a group treated with a field-cultivated ginseng extract [*: $p<0.05$, **: $p<0.01$ vs. control group; #: $p<0.05$ vs. group treated with field-cultivated ginseng extract]
Figure 6:
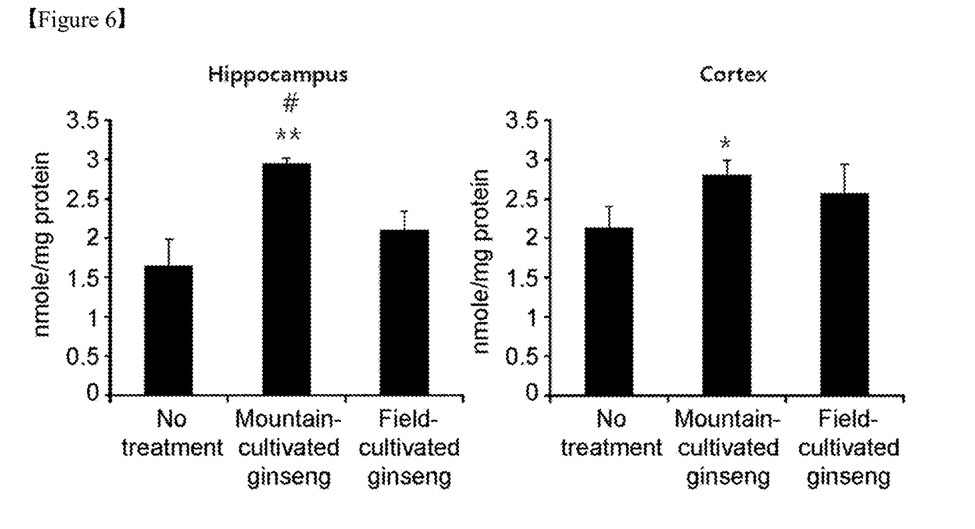
FIG. 6 is a graph showing the results of measurement of the acetylcholine level (Ach level) in hippocampi and cortexes of a control group, a group treated with a mountain-cultivated ginseng extract, and a group treated with a field-cultivated ginseng extract [*: $p<0.05$, **: $p<0.01$ vs. control group; #: $p<0.05$ vs. group treated with field-cultivated ginseng extract]
Figure 7:
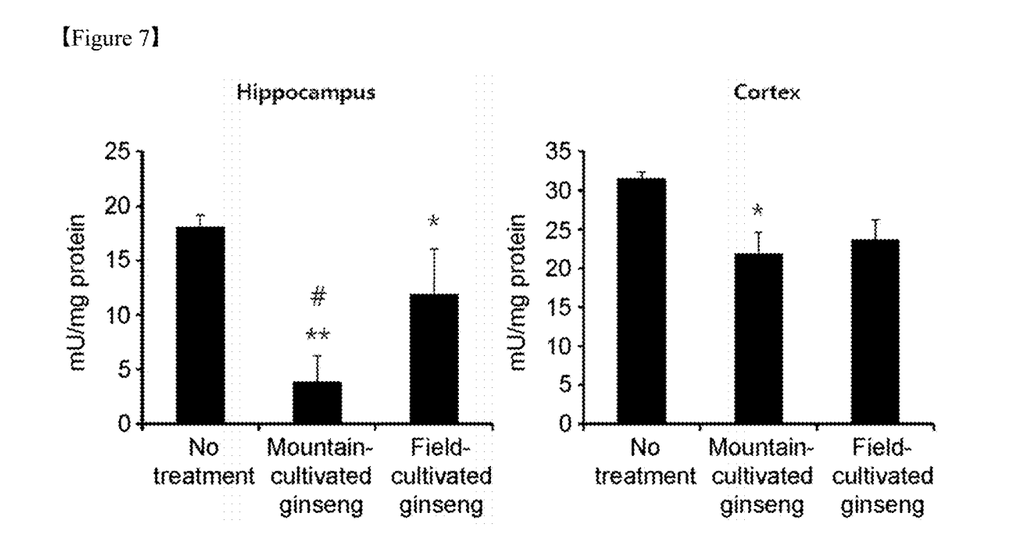
FIG. 7 is a graph showing the results of measurement of the acetyl cholinesterase activity (AchE activity) in hippocampi and cortexes of a control group, a group treated with a mountain-cultivated ginseng extract, and a group treated with a field-cultivated ginseng extract [*: $p<0.05$, **: $p<0.01$ vs. control group; #: $p<0.05$ vs. group treated with field-cultivated ginseng extract]

(4) Measurement of Choline Acetyltransferase Activity, Acetylcholine Level, and Acetyl Cholinesterase Activity Administration of the mountain-cultivated ginseng extract to the mouse significantly increased the acetylcholine concentration ($P<0.05$) and the activity of choline acetyltransferase, which is an acetylcholine synthetase, ($P<0.05$) in the hippocampus tissue, but significantly decreased the activity of acetyl cholinesterase ($P<0.05$) compared to the field-cultivated ginseng extract, which means an increase in the function of cholinergic nervous systems of the hippocampus (FIGS. 5 to 7). The results indicate that the mountain-cultivated ginseng extract has significant pharmacological efficacy in improving the function of the cholinergic nervous system of the hippocampus compared to the field-cultivated ginseng extract.

(5) Immunohistochemistry of Microglia

Figure 8A:
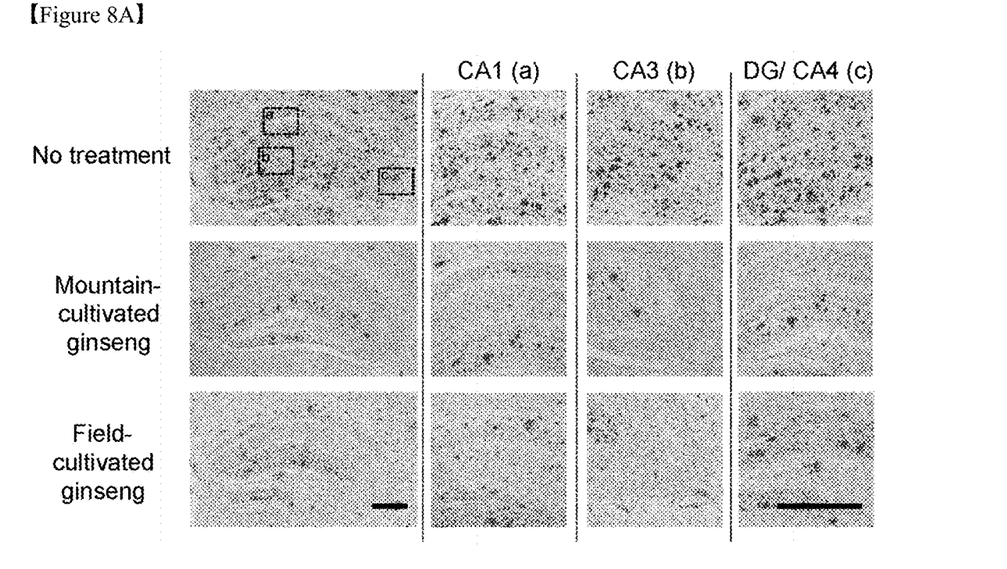
FIGS. 8A and 8B are a photograph and a graph showing the pharmacological effects of a mountain-cultivated ginseng extract and a field-cultivated ginseng extract on a Iba-1-IR positive reaction of microglia in hippocampus and cerebral cortex tissues of APPswe/PS1dE9 double-expressing mouse [*: $p<0.01$ vs. control group; #: $p<0.05$ vs. group treated with field-cultivated ginseng extract]
Figure 8B:
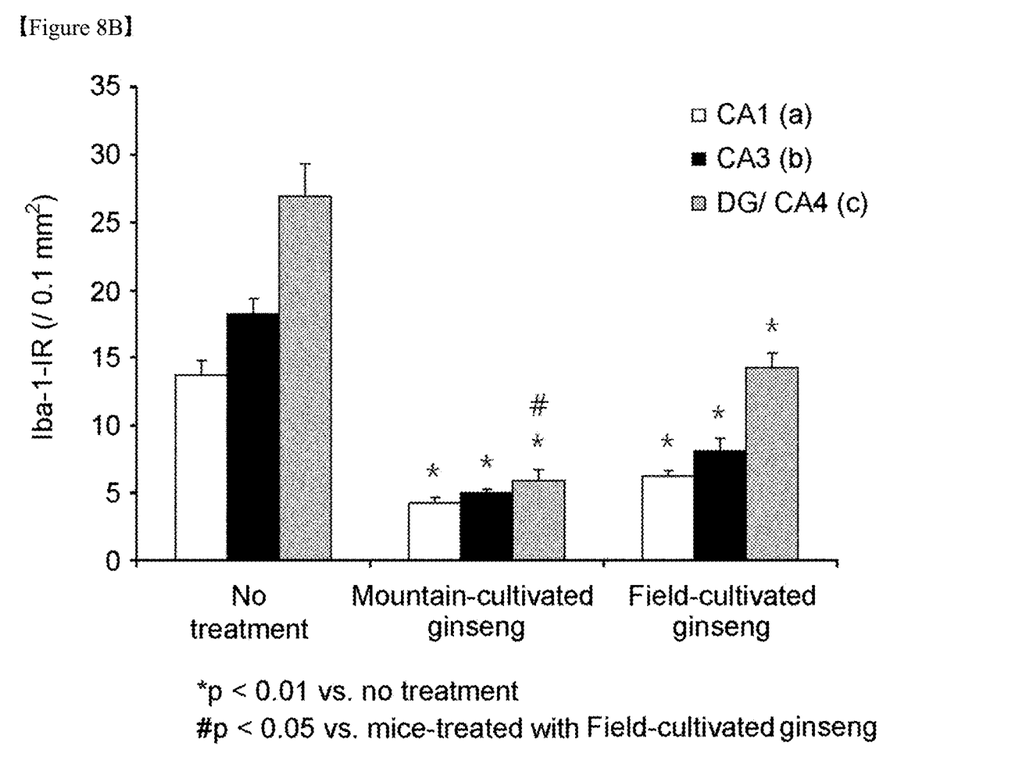

The result of measurement of the Iba-1-IR positive reaction of microglia in the hippocampus and cerebral cortex tissues of the APPswe/PS1dE9 double-expressing mouse using an immunohistochemical staining method shows that the administration of the mountain-cultivated ginseng extract significantly inhibited the Iba-1-IR positive reaction compared to the field-cultivated ginseng extract (FIGS. 8A and 8B).

(6) Beta-Amyloid

Figure 9A:
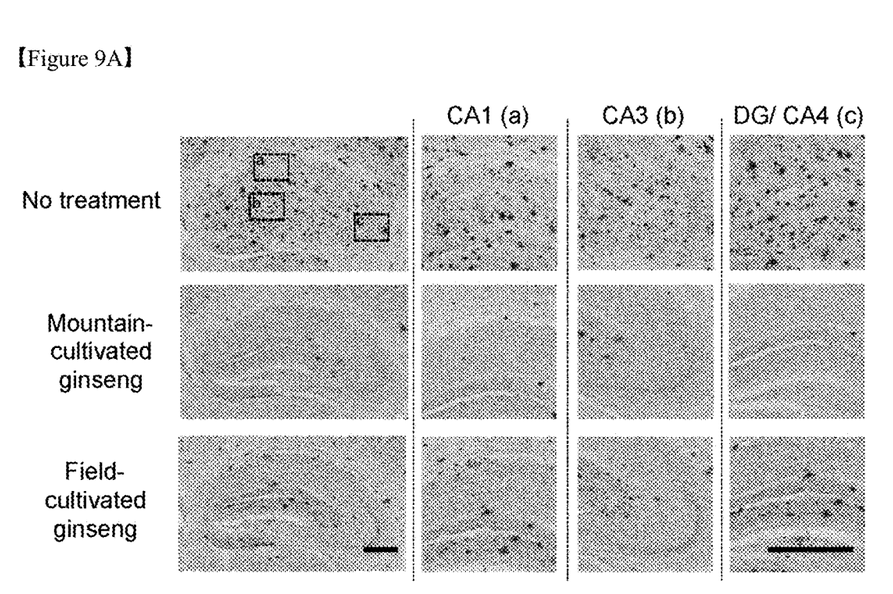
Figure 9B:
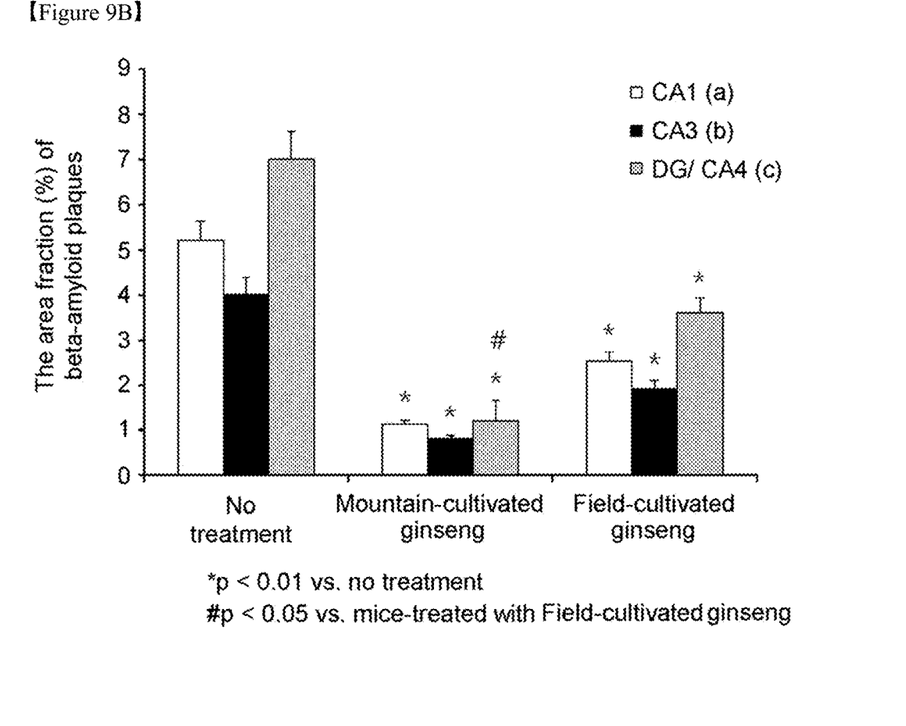

The result of measurement of the production of amyloid plaque in the hippocampus and cerebral cortex tissues of the APPswe/PS1dE9 double-expressing mouse using an immunohistochemical staining method shows that administration of the mountain-cultivated ginseng extract significantly inhibits the production of amyloid plaque compared to the field-cultivated ginseng extract (FIGS. 9A and 9B).

The invention claimed is:

1. A method for treating Alzheimer's disease or relieving symptoms of Alzheimer's disease, comprising: administering to a subject in need thereof a composition comprising a mountain-cultivated ginseng extract as an active ingredient, wherein the ginseng extract is a mixed solvent extract of mountain-cultivated ginseng obtained by the method comprising:
extracting a mixture of mountain-cultivated ginseng and ethanol in the ratio of 1.5:20 (kg:L) at 65° C. for 48 hours with an ultrasonic treatment and obtaining a first filtrate followed by a first filtering,
extracting a mixture of the mountain-cultivated ginseng residue obtained by the first filtering and distilled water in the ratio of 1.5:20 (kg:L) at 100° C. for 10 hours and obtaining a second filtrate followed by a second filtering, and
adding the second filtrate to the first filtrate.

2. The method of claim 1, wherein the Alzheimer's disease exhibits an Iba-1-IR positive reaction or production of amyloid plaque.

3. The method of claim 1, wherein the composition is a food composition for relieving symptoms of Alzheimer's disease.

4. The method of claim 1, wherein the composition is a pharmaceutical composition for treating Alzheimer's disease.

\* \* \* \* \*